United States Patent
Wollschlaeger

(10) Patent No.: US 6,409,668 B1
(45) Date of Patent: Jun. 25, 2002

(54) DEVICE AND METHOD FOR EXAMINING FEMALE BREASTS USING ULTRASOUND

(76) Inventor: Helmut Wollschlaeger, Gabrielistrasse 9, 90480 Nuremberg (DE)

(*) Notice: Subject to any disclaimer, the term of this patent is extended or adjusted under 35 U.S.C. 154(b) by 0 days.

(21) Appl. No.: 09/673,942

(22) PCT Filed: Apr. 22, 1999

(86) PCT No.: PCT/DE99/01210

§ 371 (c)(1),
(2), (4) Date: Dec. 18, 2000

(87) PCT Pub. No.: WO99/55234

PCT Pub. Date: Nov. 4, 1999

(30) Foreign Application Priority Data

Apr. 24, 1998 (DE) .......................................... 198 18 226

(51) Int. Cl.$^7$ ................................................ A61B 8/00
(52) U.S. Cl. ..................................................... 600/443
(58) Field of Search .................................. 600/407, 437, 600/439, 443–447; 601/2, 3, 4; 73/620, 612, 625, 626, 621; 128/915

(56) References Cited

U.S. PATENT DOCUMENTS

| | | | |
|---|---|---|---|
| 4,272,991 A | | 6/1981 | Cribbs |
| 4,478,083 A | | 10/1984 | Hassler et al. |
| 4,485,819 A | * | 12/1984 | Igl ............................... 128/915 |
| 5,709,206 A | * | 1/1998 | Teboul .......................... 128/915 |
| 5,999,836 A | * | 12/1999 | Nelson et al. ............... 600/407 |

FOREIGN PATENT DOCUMENTS

| | | |
|---|---|---|
| DE | 8010553 | 8/1980 |
| DE | 3015837 | 11/1980 |
| DE | 3002067 | 7/1981 |
| DE | 3224290 | 12/1983 |
| DE | 3503477 | 8/1985 |
| GB | 2015732 | 9/1979 |

OTHER PUBLICATIONS

Moskalik A. et al., "Registration of Three–Dimensional Compound Ultrasound Scans of the Breast for Refraction and Motion Correction" Ultrasound in Medicine and Biology, vol. 21, No. 6, Jan. 1, 1995, pp. 769–778, XP002060900 ISSN: 0301–5629.

Ange Hernandez et al., "Acquisition and Steroscopic Visualization of Three–Dimensional Ultrasonic Breast Data", IEEE Transactions on Ultrasonics, Ferroelectric, and Frequency Control, vol. 43, No. 4, Jul. 1996.

M. Friedrich et al., "Clinical Experience with Ultrasonic Reflection Computer Tomography of the Breast", pp. 298–303.

* cited by examiner

*Primary Examiner*—Marvin M. Lateef
*Assistant Examiner*—Ari M. Imam
(74) *Attorney, Agent, or Firm*—Jordan and Hamburg LLP

(57) ABSTRACT

The invention relates to a device and method for examining female mammals using at least one displaceable ultrasonic transducer which is disposed for scanning level layer areas and with which ultrasonic beams can be injected into at least one mammal via a coupling medium. The or each ultrasonic transducer can be displaced on a predetermined path length by means of a transporting unit so that three-dimensional ultrasound images which are electronically filed in a storage area can be generated by a computer-aided assignment of a data value, said value corresponding to the offset, to each layer image of an image sequence of layer levels of the or ski each mammal, said levels running parallel to one another. In order to reduce artifacts, differential images are calculated which are then subtracted from the original ultrasound image in a sign-specific manner. In addition, ultrasound images which are recorded by a variably tilted linear scanner are mapped on a common coordinate system or are projected in the direction of recording which is determined by the angle of tilt. Afterwards, said images are freed of artifacts min the same manner by means of a subtraction method.

3 Claims, 18 Drawing Sheets

DEVICE AND METHOD FOR EXAMINING FEMALE BREASTS USING ULTRASOUND

Figure 1:
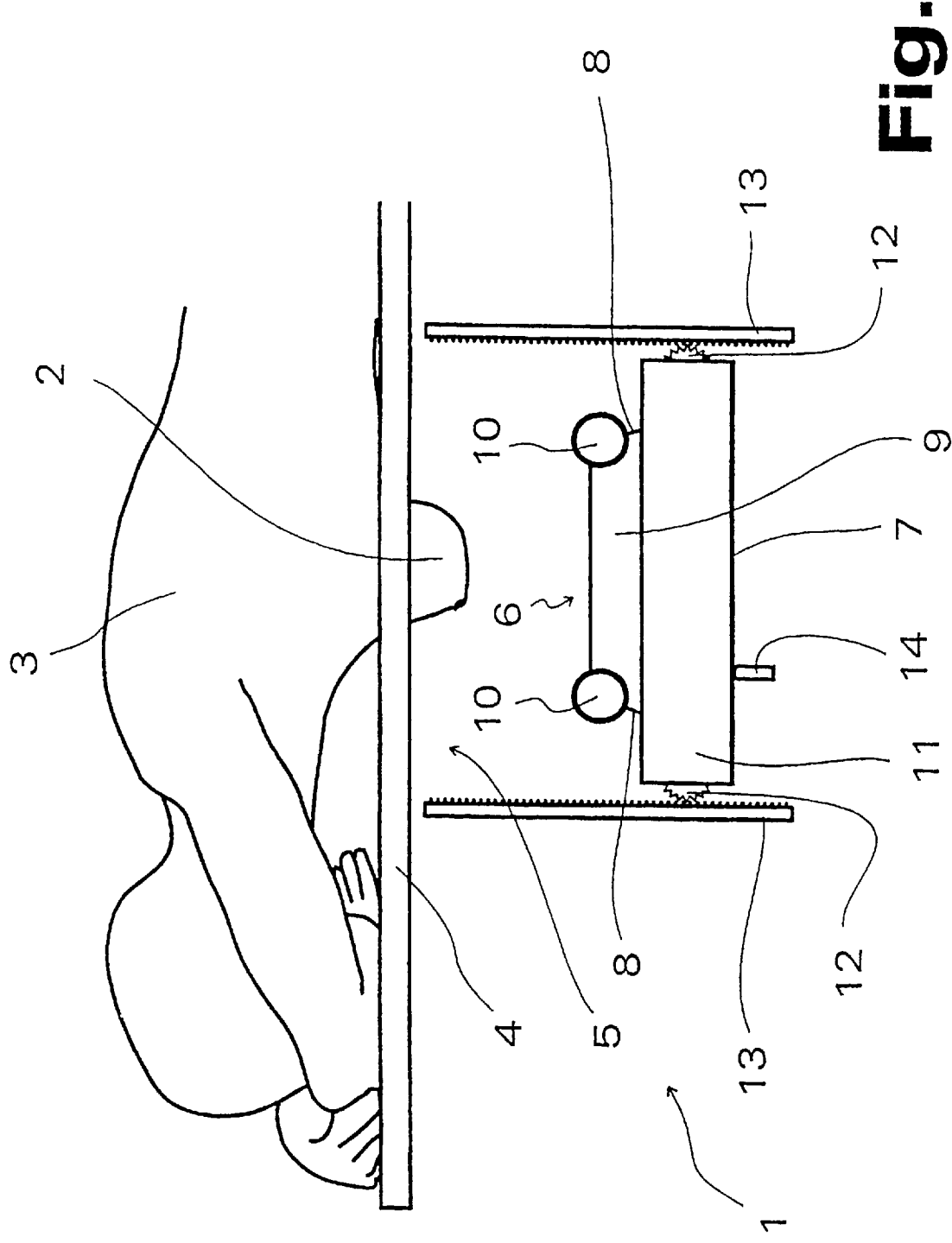

The invention relates to an apparatus for examining female breasts with at least one ultrasonic transducer for scanning level layer areas in a stationary scanning position, with which ultrasonic beams can be coupled into at least one breast over a coupling medium, and to a transporting unit for displacing the or each ultrasonic transducer between scanning positions by a pre-determined path length.

The invention furthermore relates to a method for reducing artifacts of an ultrasonic image at least of a female breast, for which an ultrasonic transducer, for scanning level layer areas in a stationary scanning position, is shifted over at least the one breast by a transporting unit by a fixed path length between scanning positions and by consecutively shifting and a three-dimensional ultrasonic image is recorded and stored in an assigned memory unit by consecutively shifting and assigning a data value, corresponding to the shifting, to a layer image of an image sequence.

Such an apparatus and such a method are already known from the article "Acquisition and Stereoscopic Visualization of Three-Dimensional Ultrasonic Breast Data" by A. Hernandez, O. Basset, I. Dautraix et al., published in the journal IEEE Transactions on Ultrasonics, Ferroelectrics, and Frequency Control, volume 43, Jul. 1996, pages 576 to 580. The article discloses an apparatus with an ultrasonic transducer, which is set up to record two-dimensional layer images and can be shifted by means of a transporting unit by a specified path length between scanning positions, in which the scanning of the two-dimensional image takes place. The disclosed apparatus furthermore comprises a memory unit for storing the layer images recorded by the ultrasonic transducer, a data value, corresponding to the shifting, being assigned. By means of this assigning, a three-dimensional ultrasonic image is produced by the disclosed recording method and stored in the memory unit. For the stereoscopic representation of the three-dimensional ultrasonic image recorded, two different three-dimensional views of the object examined are calculated starting out from a single data set stored in the memory unit and in each case assigned to one eye of the viewer, in order to make possible a three-dimensional visual perception of the ultrasonic image to this viewer.

However, the occurrence of artifacts, which cannot be differentiated in the recorded images from the real, reflecting structures of the object examined, is a disadvantage. In particular, when direction-dependent effects in the form of tail-like image patterns occur, there is a need to check the photograph for genuineness, since direction-dependent effects may be indications of pathological changes in the tissue investigated. Furthermore, the tail regions of the direction-dependent image patterns remain hidden to a viewer, since they lie, for example, behind strongly reflecting structures in the sound beam direction and do not generate any visible reflections.

In the DE 35 03 477 A1, an ultrasonic diagnosis device is disclosed, which comprises a rod-shaped linear scanner with piezoelectric elements disclosed next to one another. The linear scanner can be shifted in its transverse direction by a specified path length by means of a transporting unit. By means of the consecutive shifting of the linear scanner between scanning positions and the subsequent synchronized reading of its piezoelectric elements, sectional images in the longitudinal direction of the linear scanner, as well as sections at right angles to this of a breast, which is to be examined, can be represented on a screen unit. Here also, the frequently occurring artifacts make a medical evaluation of the ultrasonic images difficult. Furthermore, regions, lying behind strongly reflecting or reinforcing particles in the direction of the sound ray, remain hidden to the viewer.

In the DE 30 02 067 A1, an apparatus is disclosed, which permits an essentially fully automatic examination of a female breast. The apparatus comprises a couch with a resting surface, in which an opening has been provided. On the side of the couch, averted from the resting surface, a container is disposed, which is filled with water as coupling medium. Furthermore, a holding arm with at least one ultrasonic transducer is provided in the container. The holding arm is driven mechanically or electrically and carries out a semicircular swiveling motion, the center of which corresponds approximately to the center of the opening in the couch or is a few centimeters perpendicularly above the center of the plane of the opening in the interior of the thorax of the patient. During a swiveling motion of the holding arm carrying the or each ultrasonic transducer, a two-dimensional, level layer image is produced and stored in a memory unit. Furthermore, a transporting unit is provided for shifting the or each ultrasonic transducer, perpendicularly to the plane of swiveling of the holding arm or to the rotation of the swiveling plane about a common axis, by in each case a predetermined path length, so that series of level sectional images can be stored in a memory unit together with an assigned data value, corresponding to the respective shifting.

During the swiveling motion of the or each ultrasonic transducer about the breast, layer regions are scanned repeatedly, so that, because of the redundancies, averaging methods are required for representing the image. Admittedly, this method brings about a reduction in the interfering artifacts and permits all neighboring regions of strongly reflecting or reinforcing particles to be viewed. However, the occurrence of tail-like image patterns in two-dimensional sectional images, which is desirable with respect to a simplified diagnosis, is suppressed almost completely due to the averaging of the recording. Furthermore, the long measuring time of the apparatus disclosed here is a disadvantage, since the or each ultrasonic transducer, for recording a two-dimensional sectional image, already must be passed on a semicircular path about the breast, which is to be examined. Moreover, the movement of the holding arm causes a displacement, which in turn leads to a movement of the breast to be examined and, with that, to a deterioration in the quality of the layer image recorded.

From the DE 30 15 837 A1, an ultrasonic imaging apparatus with an ultrasonic transducer device is known, which has separate transducers for sending and receiving ultrasound. The height of the disclosed transducer device can be varied and the device is disposed in a water container and has a transporting unit for shifting the transducer laterally or on a circular path around the structure, which is to be examined.

From the journal "Fortschritte auf dem Gebiet der Rontgenstrahlung (Progress in the Field of X Radiation)", 147, 3 in the year 1987 in the article "Clinical Experience with Ultrasonic Reflection Computer Tomography of the Breast" by M. Friedrich, F. Fobbe and A. Sparenberg on pages 298 to 303, a method is disclosed for which the patient, resting on a couch, immerses the breast, which is to be examined through an opening in the couch into a water bath. Furthermore, an ultrasonic transducer with four individual sound heads of different focal length is disposed in the waterbath. It is passed by a transporting unit by a predetermined path length on circular scanning paths about the breast protruding into the water bath. By shifting the ultrasonic transducer, any sectional images of the breast, which is to be investigated, can be produced. With the help of an averaging method, which is unavoidable with this scanning procedure because of redundancies, a reduction in image artifacts furthermore is made possible. Aside from the absence of tail-like image patterns due to the image averaging, the passing of the ultrasonic transducer on circular paths around the breast that is to be examined and the therewith associated long recording time, required for recording a two-dimensional sectional image, are disadvantages.

In the DE 80 10 553 U1, an ultrasonic diagnostic device is disclosed, which is provided particularly for examining the female breast and consists of a couch with a resting surface and an opening through the couch. At the side of the couch, averted from the resting surface, a container filled with water is disposed, so that the breast of the patient is immersed through the opening in the couch in the water, which has been filled into the container. Subsequently, a physician can commence to scan the breast, in that he passes conventional ultrasonic testing equipment manually along the outer wall of the container.

It is an object of the invention to provide an apparatus and a method of the type named above, which permits the genuineness of image structures, visible in ultrasonic images, to be checked particularly with respect to the direction-dependent effects, in order to increase the informative power of ultrasonic images for diagnostic purposes.

This objective is accomplished with the apparatus of the type named above owing to the fact that the or each ultrasonic transducer, for the purpose of obtaining level layer images extending at an angle to one another, is held by a tilting shaft which can be rotated by an adjustable tilting angle.

This objective is accomplished for the method of the type named above owing to the fact that the ultrasonic transducer is aligned by a rotatable tilting shaft at a tilting angle with respect to the at least one breast and stored with the assigned tilting angle and that at least two three-dimensional ultrasonic images are recorded and stored.

Scanning a breast with the assigned sound beam direction is made possible because the ultrasonic transducer is held by a tilting shaft. However, direction-dependent effects, such as shadows or reinforcing zones are retained by storing the image, which is not averaged and is recorded together with an assigned tilting angle and provide a viewer or an automatic evaluation method, which follows the measurement, with important information concerning pathological changes in the object being investigated. Moreover, artifacts and, in particular, artifacts of direction-dependent structures can be differentiated from real structures by comparing corresponding image regions of the stored data blocks. Moreover, with the help of the ultrasonic transducer, working in the so-called B mode and scanning a two-dimensional area, rapid recording and storage of three-dimensional data cubes is possible.

In the case of an advantageous embodiment of the inventive apparatus, the at least one breast can be passed through an opening in the couch, which is equipped with a resting surface. The or each ultrasonic transducer is disposed on the side of the couch, averted from the resting surface and a container, holding the coupling medium, is set up between the or each ultrasonic transducer and the at least one breast for holding the coupling medium.

In order to be able to adapt it individually to at least one breast, which is to be examined, the height of the container, holding the coupling medium, can be adjusted and the container is provided with elastic upholstery.

In an appropriate further development of the inventive apparatus, the or each ultrasonic transducer is disposed at the container holding the coupling medium and terminates flush with one side, facing the coupling medium, of a wall of the container holding the coupling medium, a volume displacement of the coupling medium as the ultrasonic transducer is shifted, being avoided.

In a preferred embodiment, an ultrasonic transducer is disposed in a sound head recess of a bottom wall of the container holding the coupling medium, which can be covered completely with coupling medium. To prevent the coupling medium running out, a flexible sealing unit is disposed at one side of the bottom wall, opposite the at least one breast. At one side of the bottom wall, facing the at least one breast, the sound head recess is bounded by a membrane permeable to ultrasound and at least one region of the bottom wall, encompassing the sound head recess, can be shifted.

In a further appropriate development, the transporting unit comprises two contacting rollers, which are disposed below the container holding the coupling medium and are set up for pressing the bottom wall against the sealing lips of the side walls of the container holding the coupling medium. The contacting rollers can be driven for rotating about a specified angle.

Advantageously, at least one ultrasonic transducer is disposed as a rodshaped linear scanner, on which a plurality of elements, generating ultrasound, are disposed next to one another. The linear scanner preferably is disposed essentially parallel to the resting surface and transversely to the longitudinal direction of the couch; it being possible to shift the whole of the bottom wall in the longitudinal direction of the couch.

In a preferred embodiment of the inventive apparatus, the linear scanner is configured so that ultrasound, sent out from it, scans two breasts when the bottom wall is shifted.

In an embodiment deviating from this, the linear scanner is equipped in such a manner, that ultrasound, sent out from it, scans one breast when the bottom wall is shifted, the linear scanner being mounted so that it can be shifted on a guiding rail transversely to the scanning direction for selecting the breast that is to be examined.

In a further development of the inventive apparatus, the linear scanner is disposed parallel to the resting surface of the couch and parallel to be the longitudinal direction of the couch, the whole of the bottom wall region being displaceable in the direction transverse to the couch.

In a further example at least one ultrasonic transducer is a sector scanner with a sector-shaped scanning region, which advantageously is displaceable with the bottom wall in the longitudinal direction of the couch, the scanning sector being aligned essentially transversely to the longitudinal direction of the couch.

At least one ultrasonic transducer of a further embodiment of the inventive apparatus is constructed as a sector scanner, which is mounted in the center of the bottom wall so that it can rotate about itself.

In an example deviating from this, at least one ultrasonic transducer is constructed as a linear scanner and disposed in a disk-shaped rotatable central region of the bottom wall, the central region being mounted rotatably by means of sealing units in the stationary region of the container holding the coupling medium.

In the case of an appropriate further development, at least one ultrasonic transducer is disposed in a side wall of the container holding the coupling medium, while in any case of an example, deviating from this, the bottom wall as well as the side wall each have an ultrasonic transducer.

Advantageously, in the case of the inventive method, the ultrasonic transducer is tilted differently for each of the three-dimensional ultrasonic images.

Advisably, the coordinates of ultrasonic image, recorded with a different tilting angle, are imaged by means of a mathematical conversion program on a common coordinate system.

In the case of an appropriate further development of the inventive method, the at least two ultrasonic images are compared by means of an evaluating program point by point by difference formation and any structures, occurring only in a single memory region, are discarded as artifacts.

Furthermore, it is appropriate to determine direction-dependent structures in the respective three-dimensional ultrasonic images by means of an evaluating program by scanning the image points in the vicinity of a fixed threshold value, to compare them with projection onto the respective scanning direction by subtraction and discard only structures, occurring in a single memory region, as artifacts.

Figure 3:
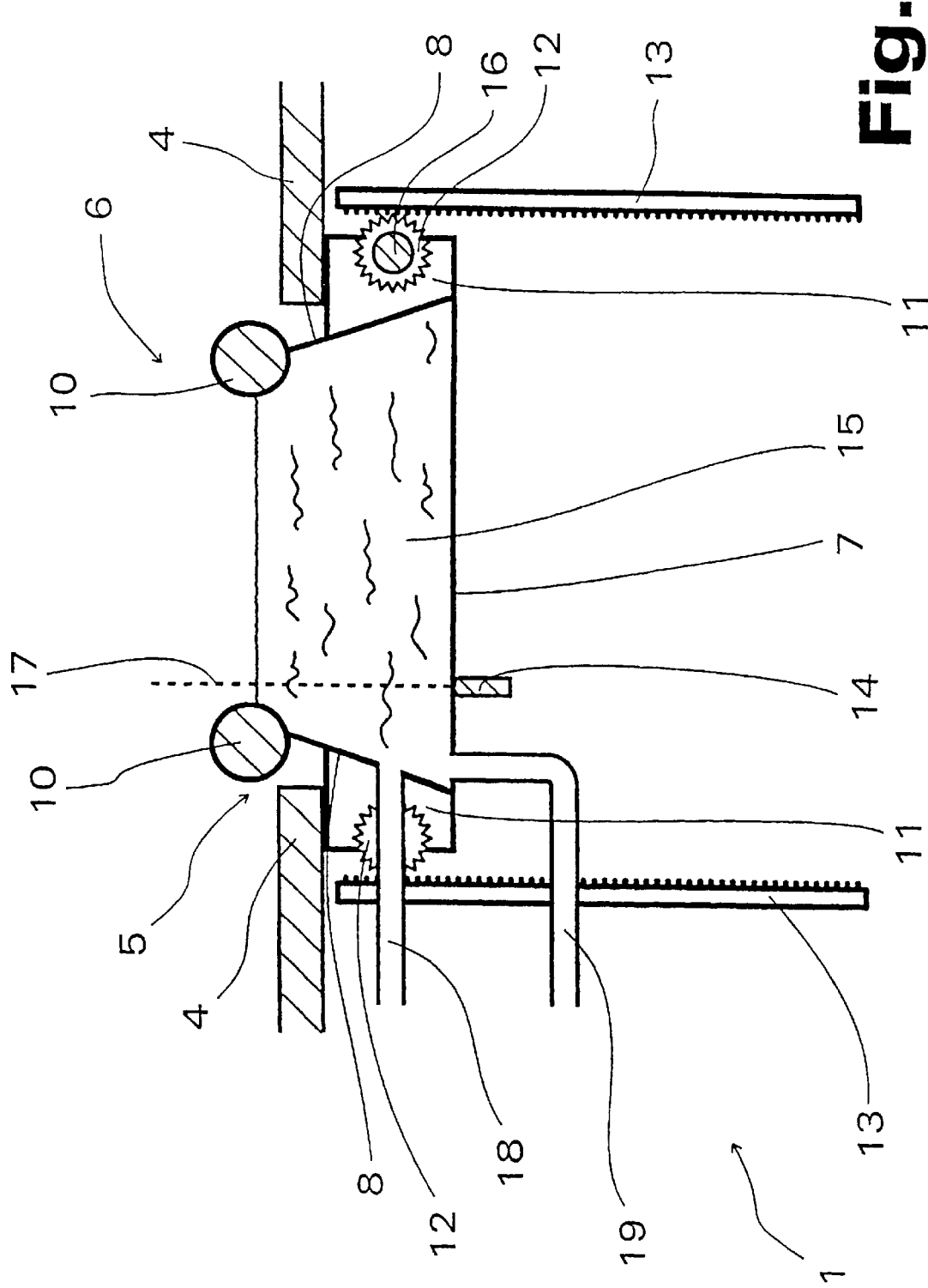
Figure 4:
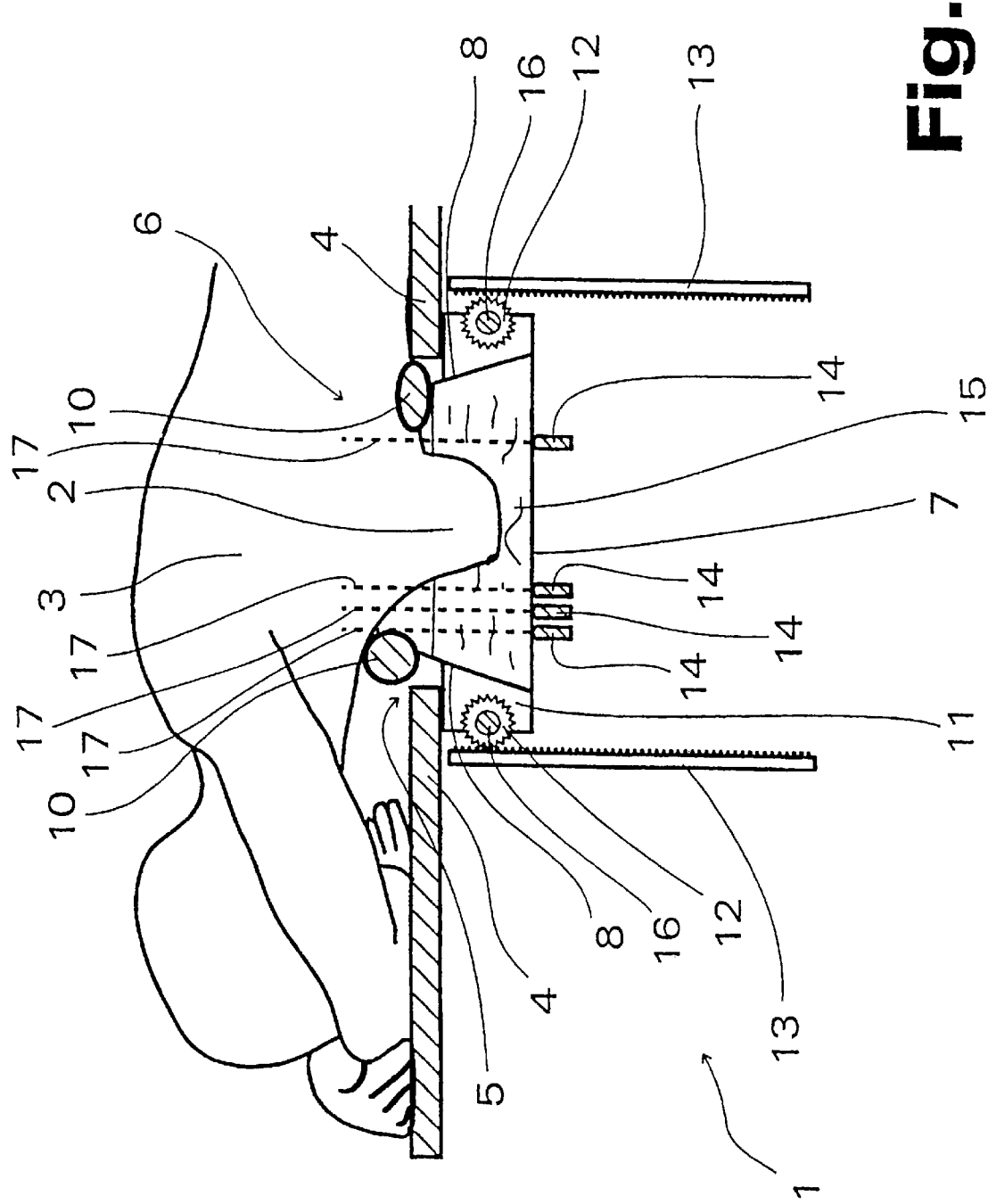
Figure 5:
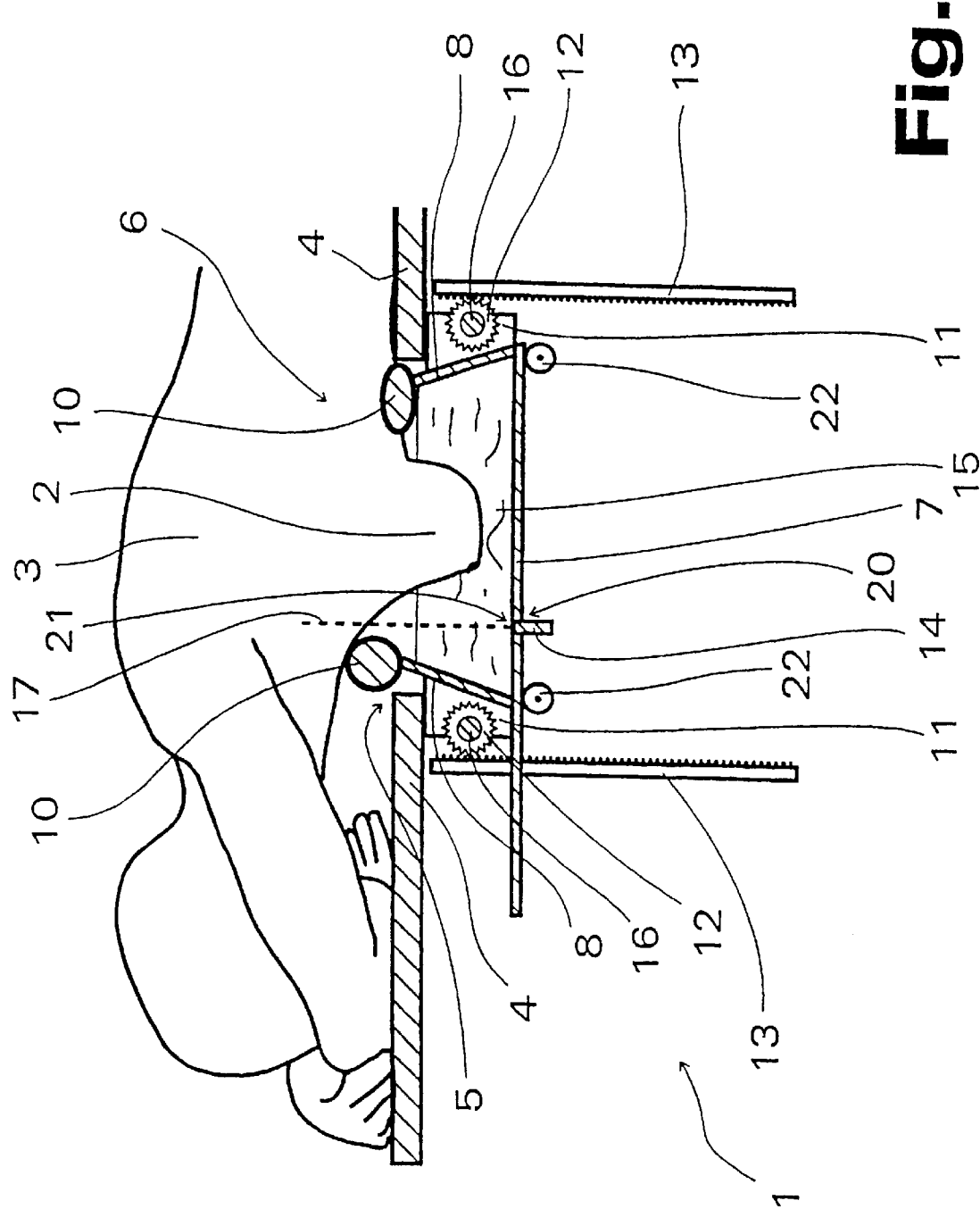
Figure 6:
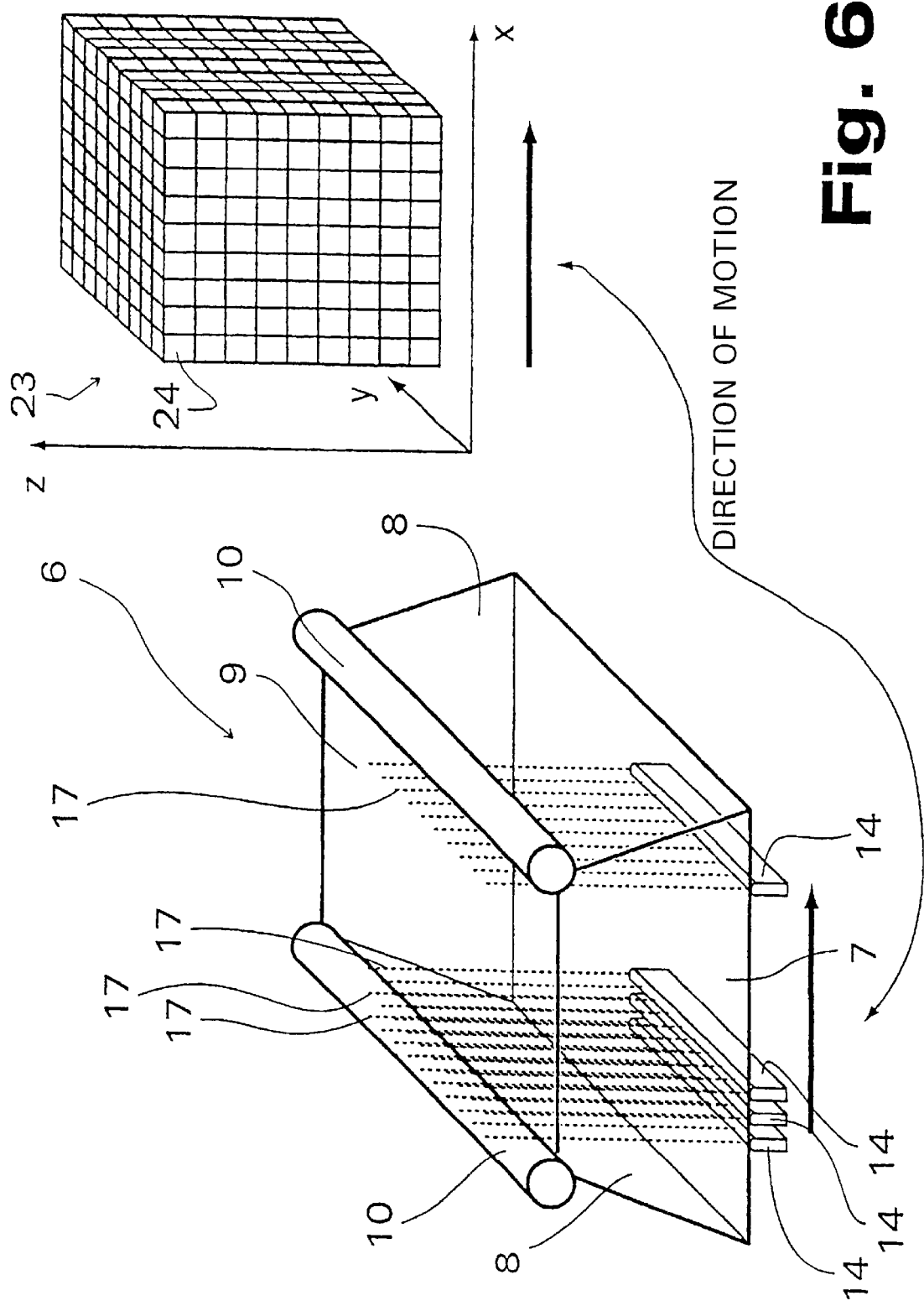
Figure 7:
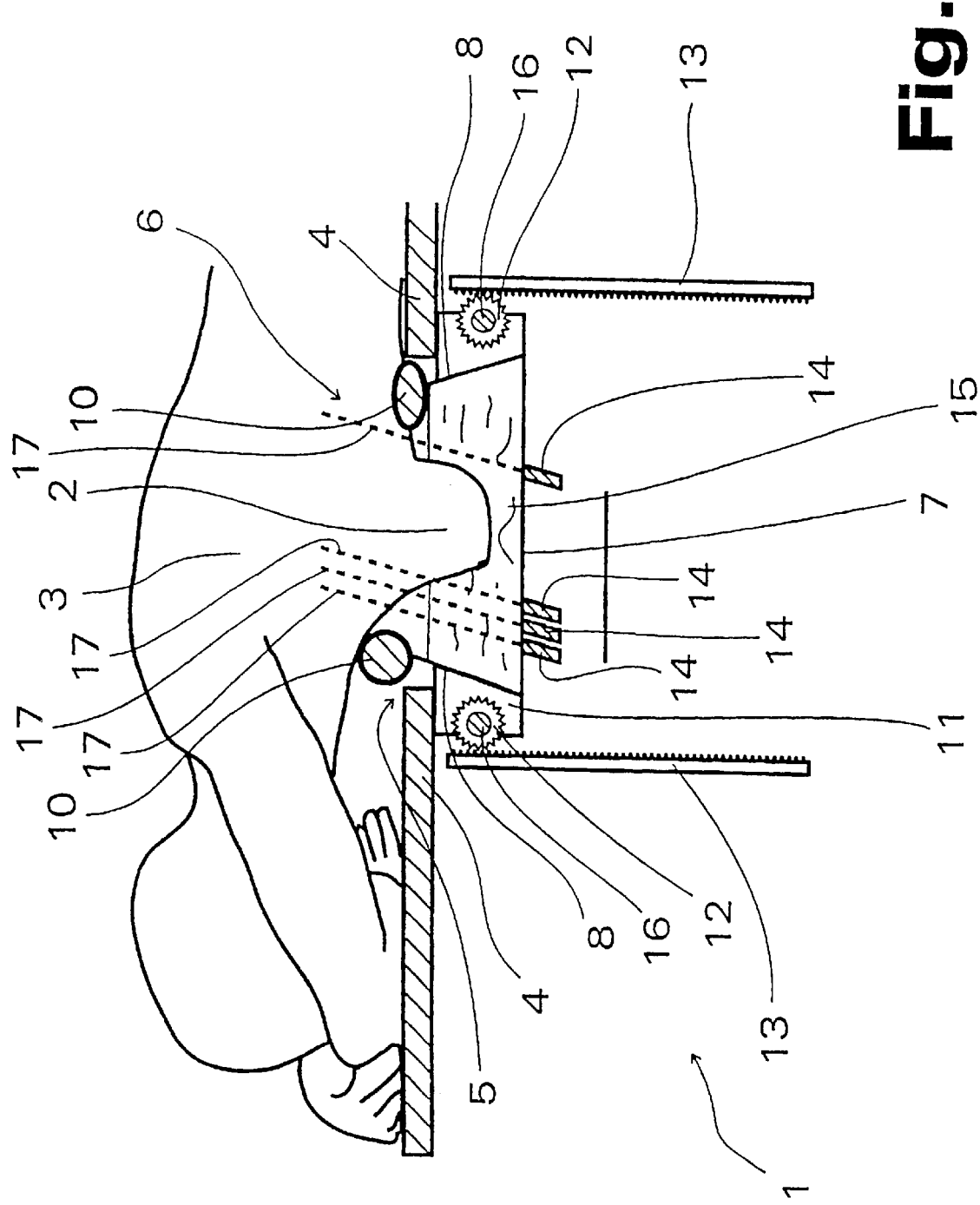
Figure 8:
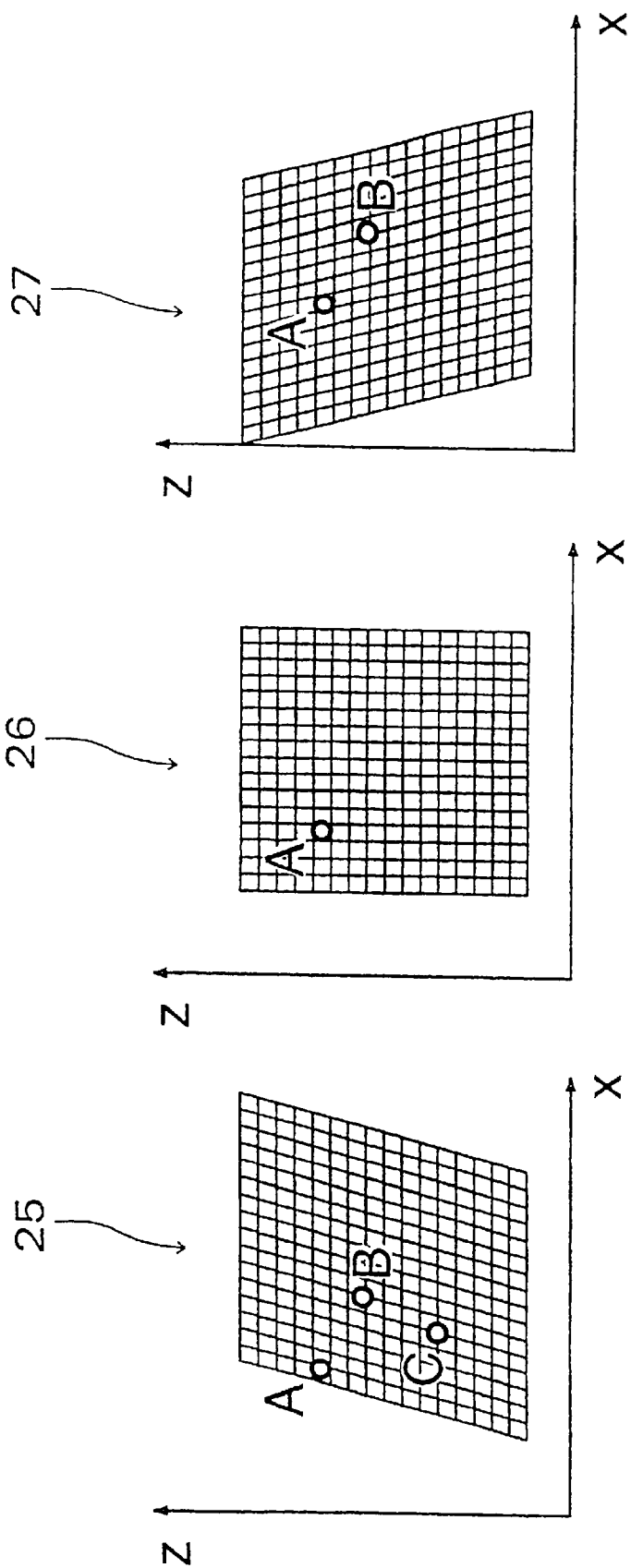
Figure 9:
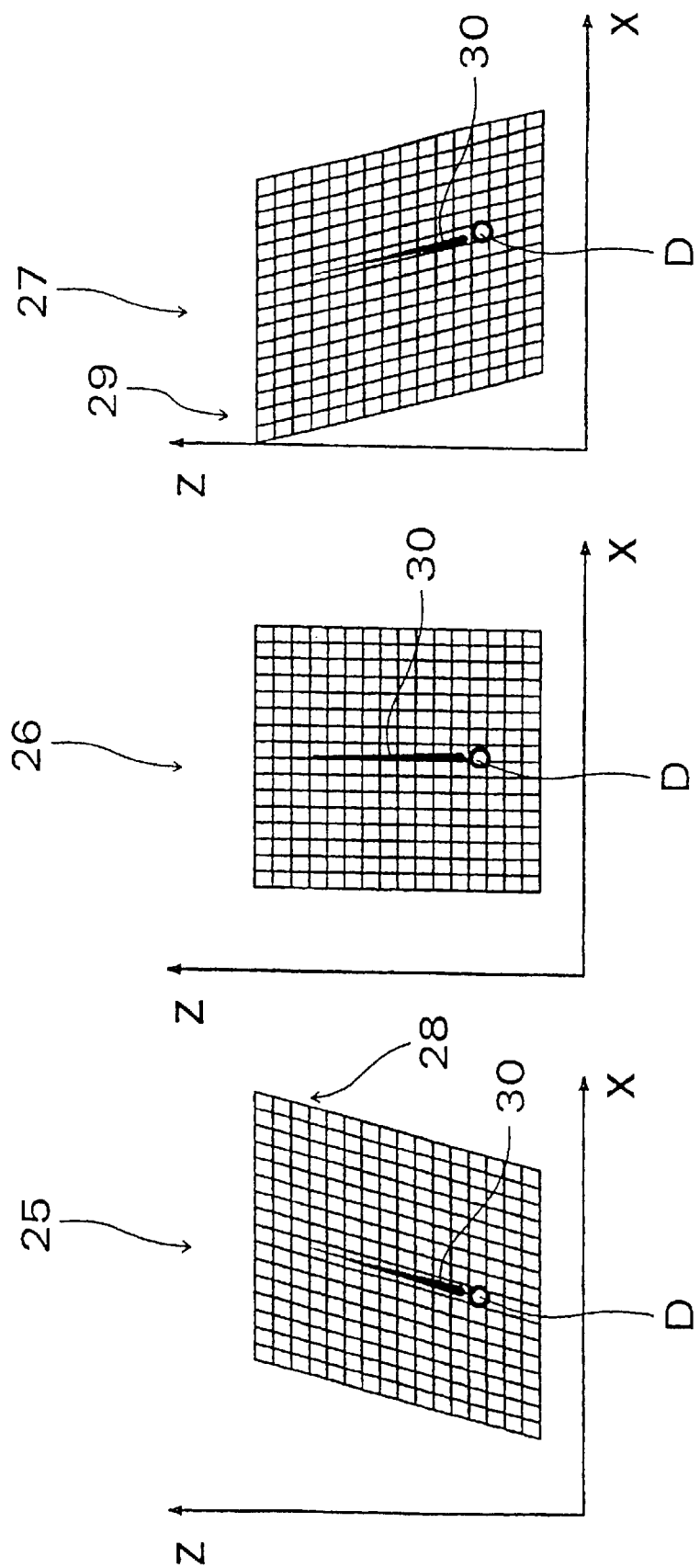
Figure 10:
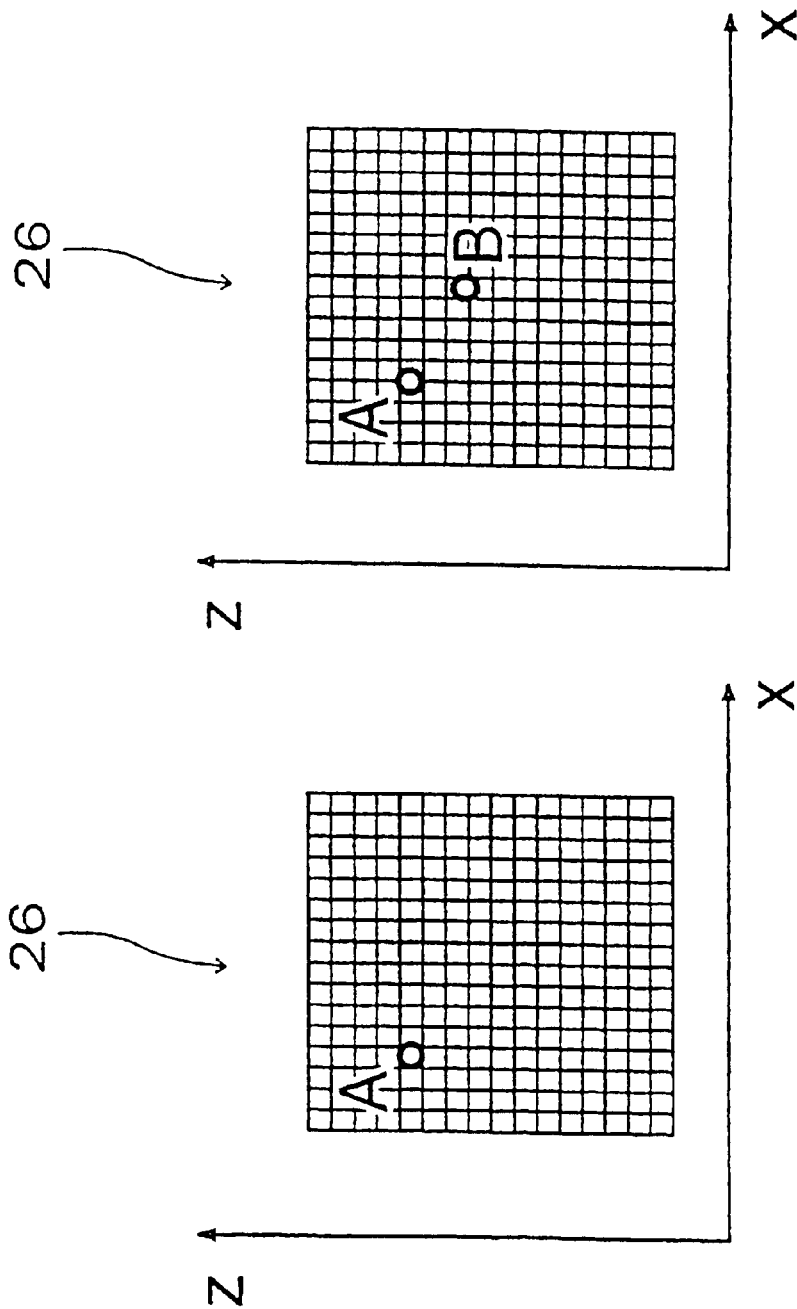
Figure 11:
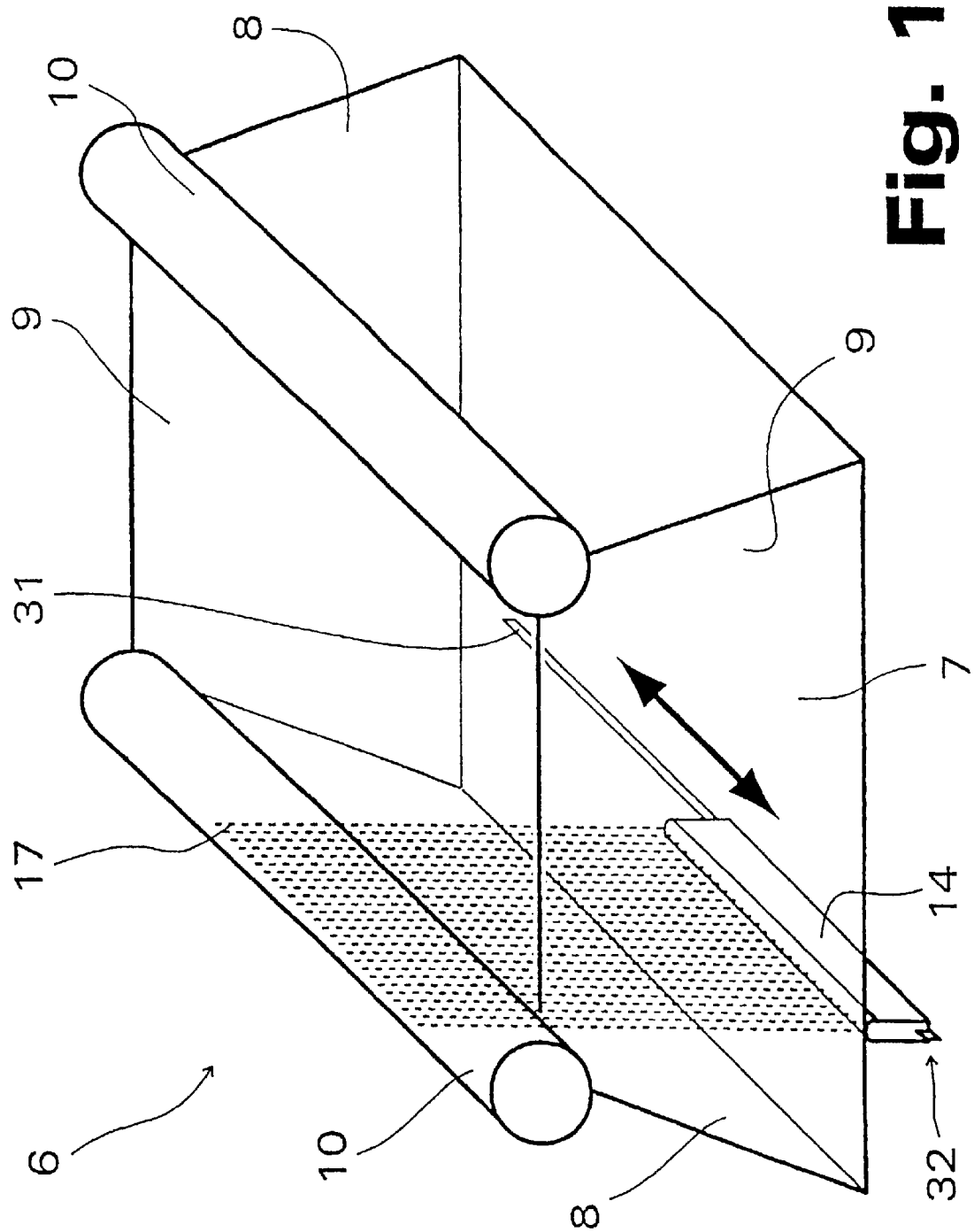
Figure 12:
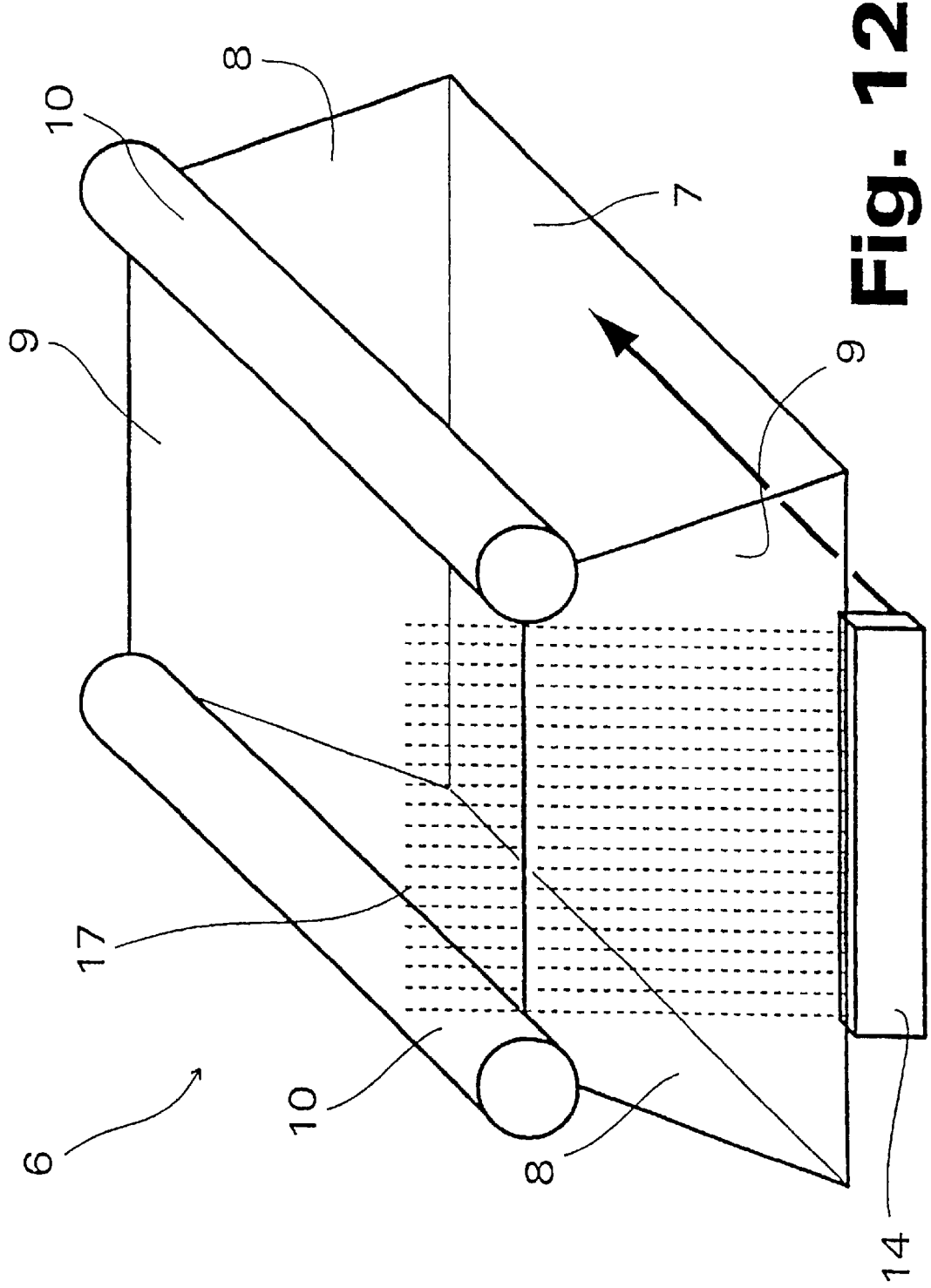
Figure 13:
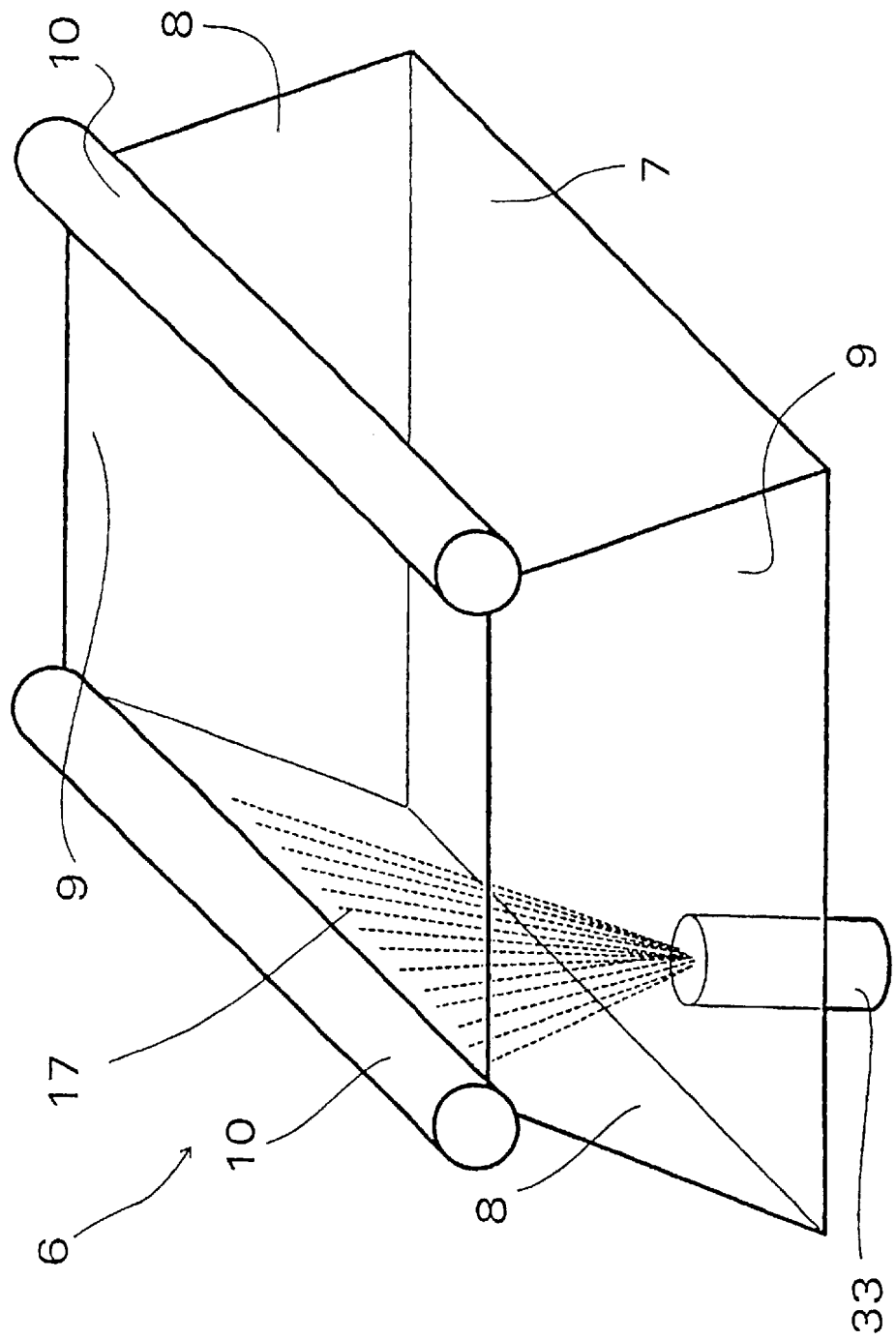
Figure 14:
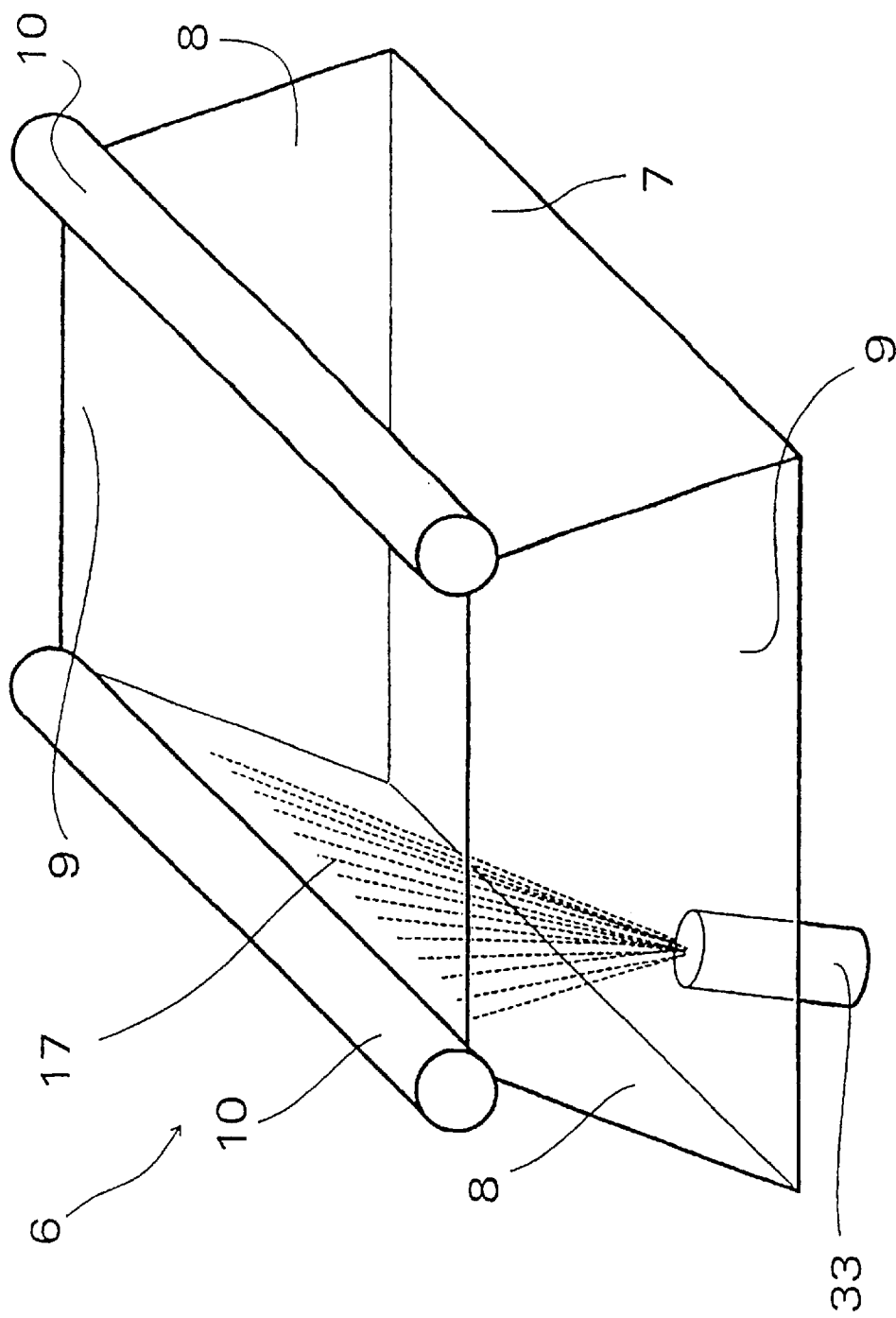
Figure 15:
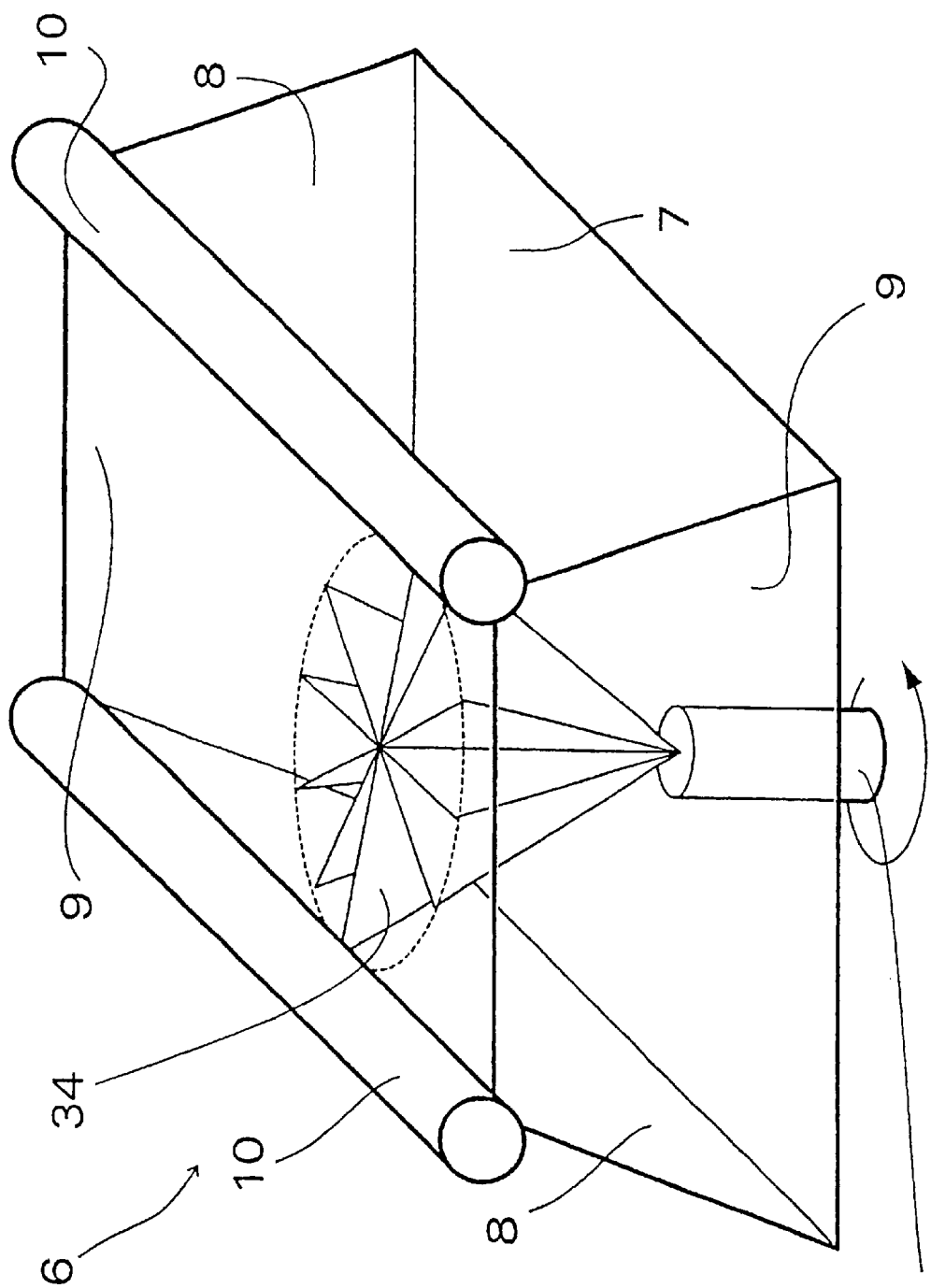
Figure 16:
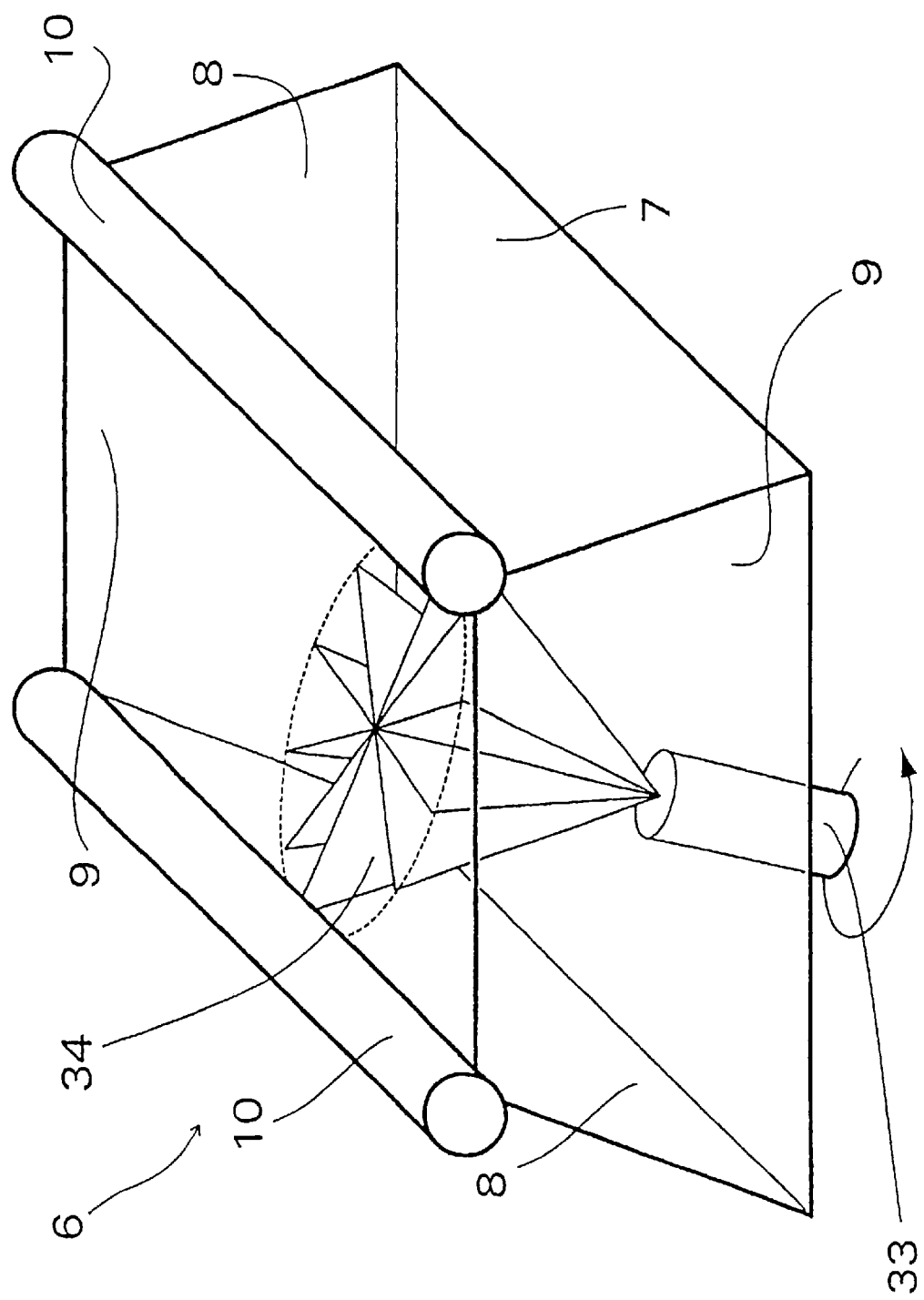
Figure 17:
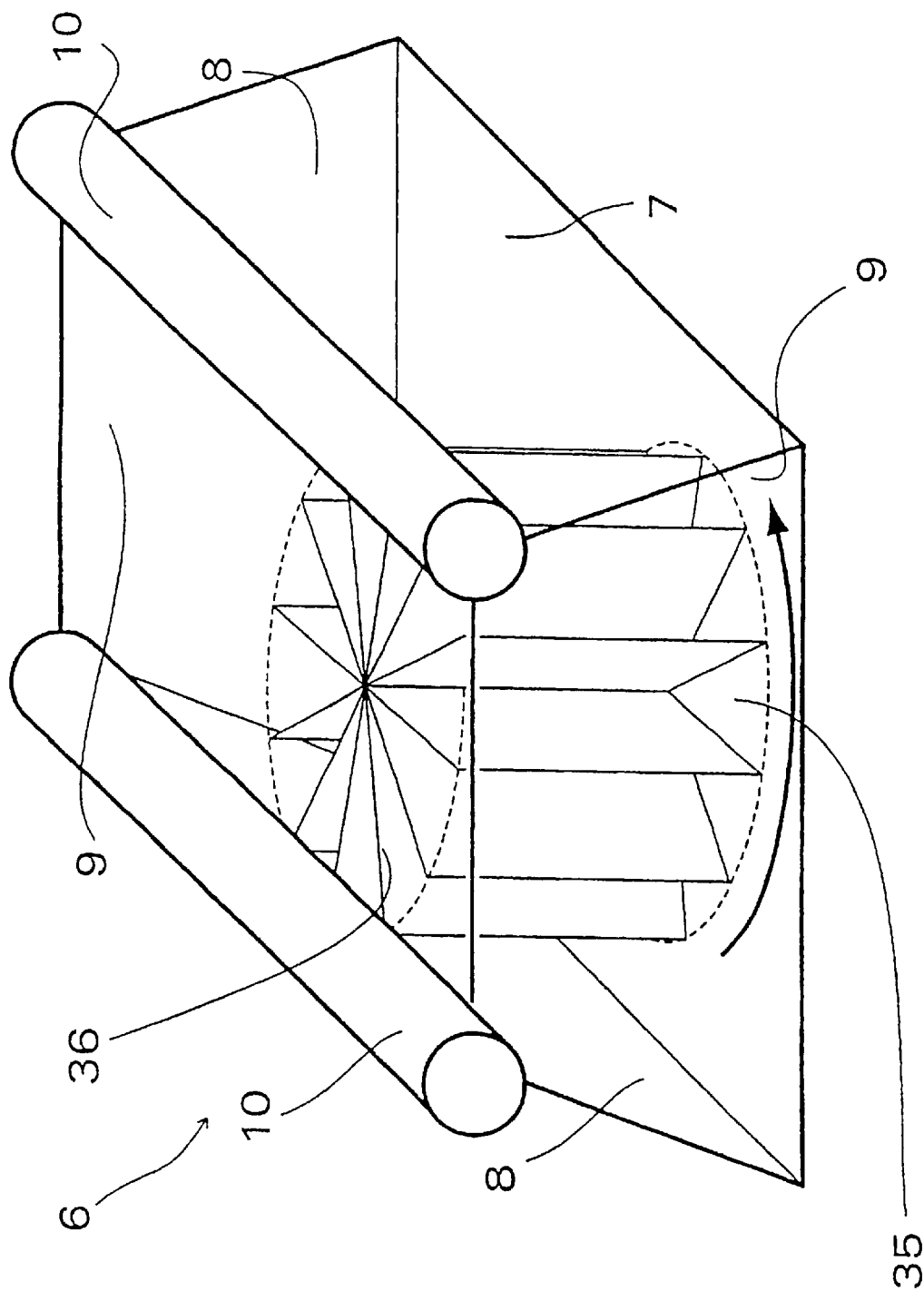
Figure 18:
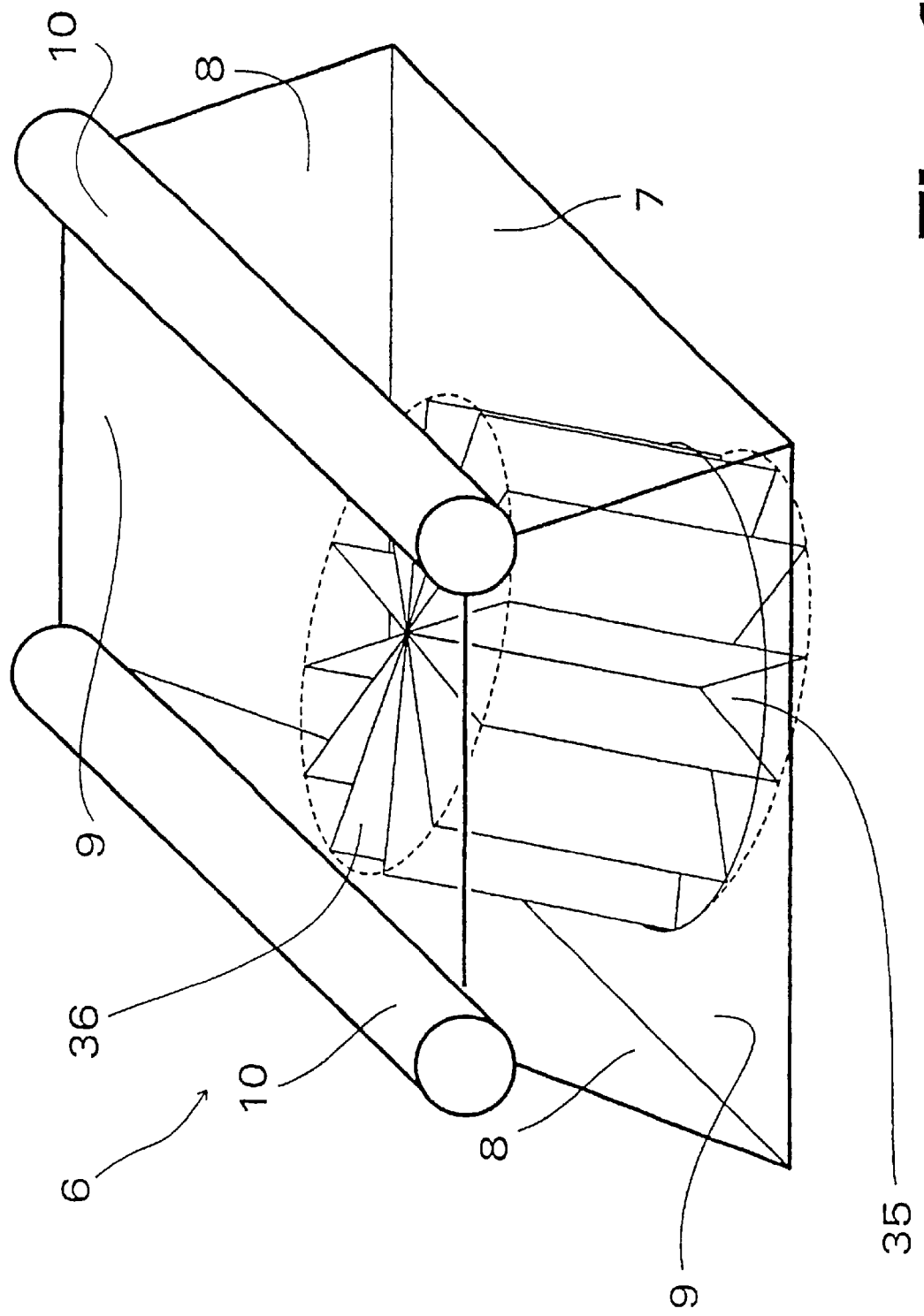

Further advantageous embodiments and advantages of the invention are the object of the following description of examples of the invention with reference to the figures of the enclosed drawing, in which corresponding components having been provided with identical reference symbols. In the drawing FIG. 1 shows a side view of an example of the inventive apparatus and of a breast, which is to be examined, before the start of the scanning, FIG. 2 shows a sectional side view of an apparatus and of a breast of FIG. 1, which is to be examined, before the start of the scanning, FIG. 3 shows a side view of an apparatus of FIG. 1 with details in addition to those shown in FIG. 2, FIG. 4 shows a sectional side view of an apparatus, illustrating different scanning positions of the ultrasonic transducer, and a breast of FIG. 1, which is to be examined, FIG. 5 shows a side view of an apparatus, cut in order to illustrate the shifting of the ultrasonic transducer, and a breast of FIG. 1, which is to be examined, FIG. 6 shows a perspective view of the container holding the coupling medium, illustrating the different scanning positions of the linear scanner, as well as a diagrammatic representation of the image data cube, obtained from the tomographic scanning, FIG. 7 shows a sectional side view of an apparatus and of a breast of FIG. 1, which is to be examined, with a tilted linear scanner in different scanning positions, FIG. 8 shows a diagrammatic representation of ultrasonic images, cut along the x–z axes and recorded with differently tilted ultrasonic transducers, FIG. 9 shows a diagrammatic representation of ultrasonic images, cut along the x–z axes and recorded with differently tilted ultrasonic transducers, to illustrate direction-dependent effects, FIG. 10 shows a diagrammatic representation of two ultrasonic images, cut along the x–z axes, FIG. 11 shows a perspective view of a container holding coupling medium, with a linear scanner to examine a single breast, FIG. 12 shows a further example of the container holding the coupling medium, with a linear scanner, which can be shifted transversely to the longitudinal direction of a couch, FIG. 13 shows a perspective view of a container holding coupling medium with a sector scanner, which can be shifted in the longitudinal direction of a couch, FIG. 14 shows a container of FIG. 12, holding coupling medium, with a tilted sector scanner, FIG. 15 shows a perspective view of a container holding coupling medium, with a sector scanner, which can be rotated about itself, FIG. 16 shows a container of FIG. 14 holding coupling medium, with a tilted sector scanner, FIG. 17 shows a perspective representation of a container holding coupling medium, with a linear scanner, which is disposed in a disk-shaped, rotatable region of the bottom wall and FIG. 18 shows a container of FIG. 17 holding coupling medium, with a tilted, disk-shaped region of the bottom wall.

FIG. 1 shows a side view of an inventive apparatus 1 and of the breasts 2 of a patient 3, which are to be examined, before the start of the examination. The patient 3 has taken up a relaxed, prone, resting position on the couch 4. The couch 4 has an opening 5, through which both breasts 2 are passed. Opposite to the freely hanging breasts 2, a container 6 holding the coupling medium is disposed and has a square bottom wall 7, side walls 8, 9 and cushioning constructed as a foam rubber cushion 10.

A housing 11 for the driving mechanism, which extends around the container 6 holding the coupling medium, is set up for adjusting the height of the container 6 holding the coupling medium and, in its lateral edge regions, has a gear wheel 12, which protrudes beyond the extent of the housing 11 of the driving mechanism. The gear wheels 12 engage the gear racks 13, which are firmly connected with the couch 4 by fastening means, which are not shown. On the side of the bottom wall 7, averted from the breasts 2, a linear scanner 14 is disposed, the mounting of which will be described in detail in the following.

Figure 2:
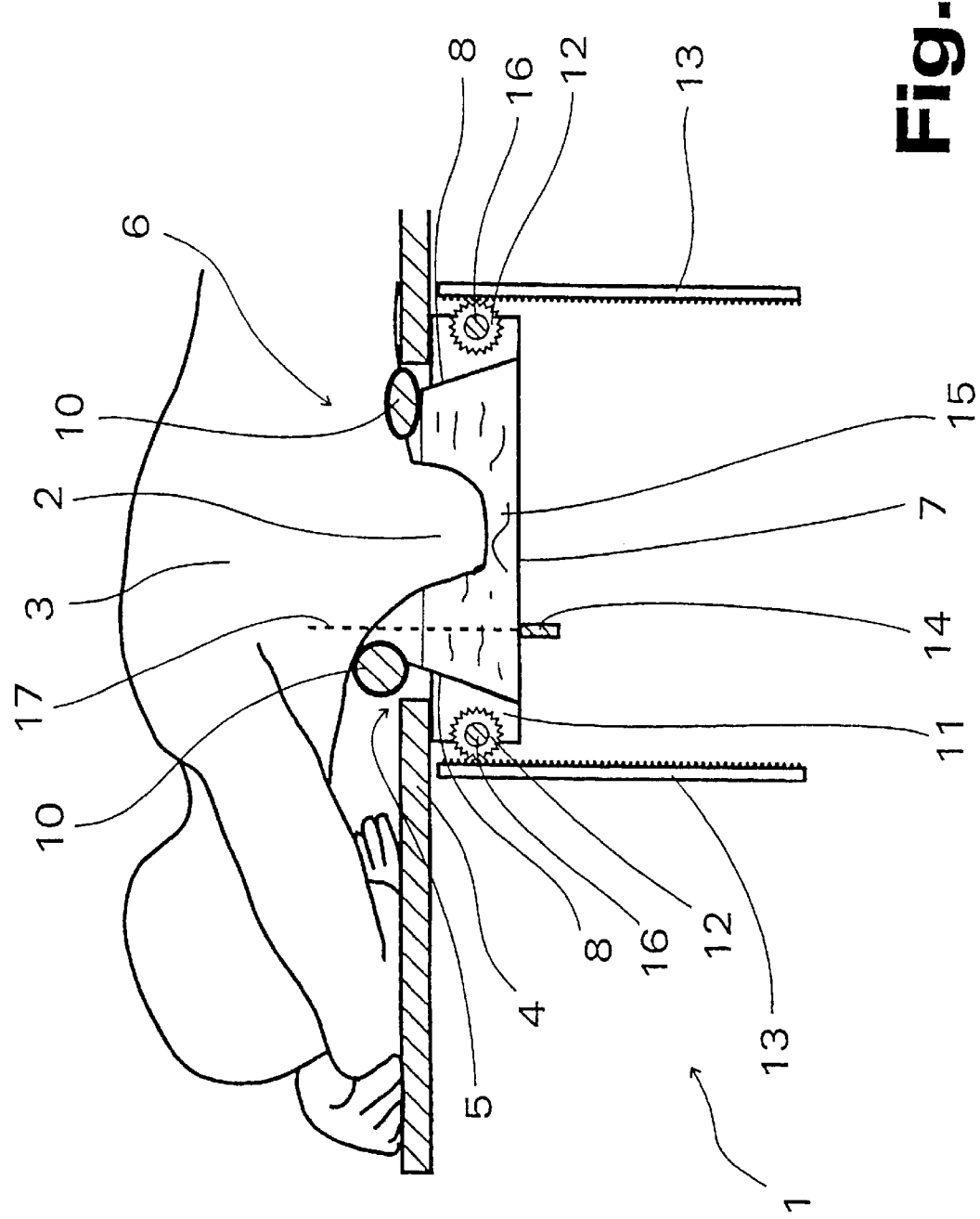

FIG. 2 shows a sectional side view of the apparatus 1 of FIG. 1 immediately behind the housing 11 for the driving mechanism, and of the breasts 2, which are to be examined, at the start of the scanning, the sectional walls of the housing 11 for the driving mechanism and of the container 6 holding the coupling medium being shown, as also in the following Figures with the exception of FIG. 5, as continuous lines.

The height of the container 6 holding the coupling medium is shifted in such a manner in FIG. 2, that both foam rubber cushions tend extends through the opening 5 in the couch and lie against the body of the patient 3. Moreover, the breasts 2 protrude into the container 6 filled with the coupling medium, which can be filled with water 15 as coupling medium. In this position, the foam rubber cushions 10, because of their high elasticity, nestle against the body of the patient 3 about the breasts 2 and seal off this region.

The gear wheels 12, which engage the gear racks 13, are connected non-rotationally with a gear wheel driving shaft 16, which extends between the side walls of the housing 11 of the driving mechanism. In order to adjust the height, the driving force, which is generated by a driving motor that is not shown, is introduced over a transfer means, which is also not shown, into the gear wheel driving shaft 16.

An ultrasonic beam 17, generated by the linear scanner 14, is directed at right angles to the wall 7 of the bottom of the container 6 holding the coupling medium and, before entering tissue, passes through a layer of water in order to reduce coupling losses. Because of the large immersion region of the breasts 2 in the water 15, images of tissue sections can also be produced in those regions, which cannot be detected by other methods of examination, such as, for example, mammography.

FIG. 3 shows a sectional side view of the apparatus 1 of FIG. 1 and illustrates, in particular, a water inlet 18, which has not been shown in the other Figures for reasons of clarity and which is used to fill the container 6, holding the coupling medium, with water 15, and a water outlet 19, which is set up for discharging the water 15. Moreover, the water outlet 19 is integrated into the bottom wall 7, so that the water 15 can drain almost completely.

FIG. 4 shows a sectional side view of the apparatus 1 of FIG. 1 and of the breasts 2, which are to be examined, several scanning positions of the linear scanner 14, which follow one another temporally during the scanning process, being represented stroboscopically.

FIG. 5 shows a sectional side view of the apparatus 1 of FIG. 1 and illustrates an example of the transporting unit for shifting the linear scanner 14. In order to avoid movement of the breasts 2 because of the flow of the water 15 during a scanning process, which preferably lasts for 4 seconds and, with that, to avoid a deterioration of the tomographically assembled three-dimensional image, the linear scanner 14 is disposed in a sound head recess 20 of the bottom wall 7 and held there by a tilting shaft, which is not shown and is mounted on the side of the bottom wall 7, averted from the breasts 2.

The sound head recess 20 is filled with water 15 and the linear scanner 14, at the side averted from the breasts 2, is secured by means of a flexible sealing composition, which is not shown, with respect to the water outlet. At the side of the bottom wall 7 facing the breasts 2, a synthetic resin membrane, which does not absorb the ultrasonic beam 17, forms of the boundary between the sound head recess 20 and the remaining water 15 of the container 6 holding the coupling medium. Due to the planar configuration of the bottom wall 7, a volume displacement and, with that, a flow motion of the water 15 during the scanning procedure is avoided.

On the side of the bottom wall 7, averted from the breasts 2, rotatable contact rollers 22 are disposed, which press the bottom wall 7 against sealing lips of the side with walls 8, which are not shown and are set up to seal the container 6 holding the coupling medium. In the example shown, the transporting unit comprises a stepper motor (not shown), force transferring means such as a belt as well as the contacting rollers 22. Moreover, the contacting rollers 22, which are driven by the stepper motor that over the force transferring means, displace the bottom wall 7 stepwise preferably by 0.5 millimeters in the longitudinal dissection of the couch 4.

To control the apparatus 1, a control program of a single terminal computer, which is not shown, is provided. To commence a scanning process, the control program instructs the contacting rollers 22 over the stepper motor to bring the linear scanner 14 into the starting position. Subsequently, the control program instructs the linear scanner 14 over data exchange leads, which are not shown, to scan a level layer of tissue. The linear scanner 14 transmits the analog image data to an analog/digital converter. The control program assigns the coordinates of the digitized two-dimensional sectional image a further coordinate value, which corresponds to the position of the linear scanner 14 in the scanning direction and stores the image data, so produced, in a previously set up area of a memory unit.

Subsequently, the control program instructs the contacting rollers 22 to shift the bottom wall 7. Once the linear scanner 14 has taken up its new scanning position, it is instructed to scanning a further tissue layer. The process is repeated until the linear scanner 14 has reached a predetermined and position. Three-dimensional ultrasonic images, stored digitally in this manner, can be archived in assigned areas of the memory.

The scanning process described typically lasts for 4 seconds, during which the patient 3 is instructed to suspend breathing as far as possible. When several scanning processes are carried out to increase the accuracy of the examination, the end position of a prior scanning process serves as the starting position for the subsequent scanning process, the subsequent movement being in the opposite direction of the prior scanning process and the three-dimensional images being archived in assigned areas of the memory unit.

FIG. 6 shows a perspective view of the container 6 holding the coupling medium, illustrating the difference scanning positions of the linear scanner 14, as well as diagrammatically a three-dimensional data cube 23, illustrating the coordinates of the ultrasonic image. In this connection, the data value plotted on the x axis corresponds to the respective scanning position of the linear scanner 14, the data value plotted on the z axis corresponds to the running time of an ultrasonic echo and, with that, essentially to the distance of the reflecting structure from the wall 7 of the bottom and the data value plotted on the why axis corresponds to the distance between the elements on the linear scanner 14, producing the sound beams, and a reference element, which advisably is one of the two outer elements of the linear scanner 14. A digital value, which consists preferably of 8 bits and corresponds to an intensity of the reflected ultrasonic beam 17, is assigned to the image data points 24 obtained in this matter.

FIG. 7 shows a sectional side view of the apparatus 1 of FIG. 1, the linear scanner 14 generating ultrasonic beam 17, which are inclined at an angle to the bottom wall 7. The angle of inclination can be adjusted by tilting the linear scanner 14 by means of the tilting shaft, which is not shown. The recording of a three-dimensional ultrasonic image with a tilted linear scanner 14 makes additional information available for the evaluation.

FIG. 8 shows a diagrammatical representation of ultrasonic images, cut along the x–z axes and recorded with a indifferently tilted ultrasonic transducer 14. A first tilted sectional image 25 corresponds to an ultrasonic image photographed with a linear scanner 14 tilted in the direction of increasing x values, a rectangular sectional image 26 corresponds to photograph with a linear scanner 14, which is not tilted and directed at right angles to the bottom wall 7 and a second tilted sectional image 27 corresponds to a photograph with a linear scanner 14, tilted in the direction of decreasing x values. The first tilted sectional image 25 has, for example, structures A, B and C, the rectangular sectional image 26 has only the structure A and the second to tilted sectional view 27 has the structures A and B. The representation of structures actually present is, however, independent of the tilting of the linear scanner 14. Accordingly, in the case shown by way of example, structure A corresponds to a structure actually present. On the other hand, structure C is an artifact occurring only during a measurement. Structure B probably is a structure actually present.

In order to decide with the help of automated methods whether the structures A, B, C photographed are real structures or parts of real structures, that is, for example, cysts or calcification particles or whether they are artifacts, the coordinates of tilted data cubes are converted by a trigonometric conversion program into coordinates of a rectangular data cube.

The Cartesian representation of all image points makes possible a computer-supported comparison of the ultrasonic images, for which a comparison program compares the digitized intensity of the reflected ultrasonic beams 17 point by point and characterizes or discards artifacts occurring only in a single memory area. During the projection of the tilted sectional images 25, 27 onto a Cartesian coordinate system and the subsequent comparison of the data values so obtained, only the data points need be considered, which lie in the common sectional amount of these sectional images 25, 26, 27. The data points 28 of the first tilted sectional image 25, which cannot be utilized and have high x and high z values, or the data values 29 of the second tilted sectional image 27, which cannot be utilized and have high z values but small x values, corresponds to regions outside of the rectangular data cube and therefore cannot be utilized for automated evaluation methods.

Further information concerning the question whether stored image data relates to real structures or artifacts is provided by direction-dependent effects.

FIG. 9 shows a first tilted sectional image 25, a rectangular sectional image 26 as well as a second tilted sectional image 27. All sectional images have a structure D, which therefore could be a real structure. Behind structure D in the photographing direction, a tail-like shadow 30 can be detected. Such a shadow 30 occurs, for example, when the ultrasonic beam 17 is reflected completely by a calcification particulates, so that ultrasound for a reflection is not available from the tissue lying behind the calcification particles in the photographing direction. If the shadow thrown depends on the direction of the recording, then this is a further indication that the photographed structure D is a real structure. The direction dependent effects accordingly represent a further differentiation method for the examination.

If direction-dependent structures are found by means of an evaluation program, the image points of a 3-dimensional ultrasonic image are scanned point by point. If a predetermined threshold value is attained by an image point, which corresponds, for example, to a known reflection value of a calcification particles, the program examines the surroundings for similar data values or image points with greatly changed the data values. If the evaluation program finds such a region, it is probably a question of a direction-dependent effect. Subsequently, the evaluation program calculates the gradient of the intensity change and the projection of the direction-dependent region onto the alignment of the ultrasonic beam 17, which is fixed by the tilting angle of the linear scanner. The projections of the different ultrasonic images are subtracted from one another, such regions, which exceed a fixed difference value, being discarded as artifacts. The calculated gradient, which should be parallel to the alignment of the ultrasonic beam 17 when structures are actually present, is a further indication of artifacts.

Moreover, the direction-dependent effects, aside from their property of differentiating real structures from artifacts, represent a cause for the tiltable construction of the linear scanner 14. The tilting enables information to be made available even in those regions, which in the case of a simple scanning process lie in the shadow region of, for example, a strongly reflecting particle.

In the case of a deviating example of the inventive apparatus, one of the sidewalls 9 of the container 6 holding the coupling medium has a second linear scanner which, like the linear scanner 14 disposed in the bottom wall 7, can be shifted by a transporting unit. Due to the inventive use of a second linear scanner, image information can also be generated from regions, which lie behind structures D throwing shadows.

FIG. 10 shows a diagrammatic a representation of two ultrasonic images 26, cut along the x–z axes. The rectangular sectional images 26, recorded with the linear scanner 14 when not tilted, jointly have a structure A. On the other hand, structure B occurs only in the sectional image 26 on the right, so that structure B is an artifact.

In order to eliminate artifacts when representing the image, a difference memory area, for storing a difference image, calculated from the difference between two image data sets, is provided in the memory unit. For example, if the left sectional image 26 is subtracted from the right sectional image 26 of FIG. 10, the difference image of the example shown contains only the structure B with the positive algebraic sign. Real structures, such as A, are contained in the difference image. If the positive image data values of the difference image are subtracted from the sectional image 26, shown to the right in FIG. 10, an artifact-free ultrasonic image is obtained.

FIG. 11 shows a perspective view of a containers 6 holding the coupling medium, with a linear scanner 14 for examining only one breast 2. In this embodiment, the containers 6 holding the coupling medium is equipped with a linear scanner 14, which passes only over one breast 2 when shifted in the longitudinal direction of the couch 4. At the side of the bottom wall 7, averted from the breast 2, a guide rail 31 is provided, which engages a guiding groove 32 of the linear scanner 14. By shifting the linear scanner 14 on the guide rail 31 with the help of shifting means that are not shown, it is possible to select whether the light or the left breast 2 of the patient 3 is scanned.

FIG. 12 shows a further example of the container 6 holding the coupling medium and provided with a linear scanner 14, which can be shifted transversely to the longitudinal direction of the couch 4. In the case of this example, the breasts 2 are scanned consecutively and not in parallel.

FIG. 13 shows a perspective view of a further example of a container 6, holding the coupling medium, with a sector scanner 33, which can be shifted in the longitudinal direction of the couch 4 and has a sector-shaped scanning profile 34. Shifting the sector scanner 33 in the indicated direction of motion brings about a wedge-shaped scanning of the breast 2.

FIG. 14 shows the container 6, holding the coupling medium, of FIG. 13 with a tilted sector scanner 33. The tilted scanning of the breast 2 enables image information to be obtained even from those regions, which lie in the shadow, for example, of highly reflecting structures in the case of a not-tilted scanning.

FIG. 15 shows a perspective view of a container 6, holding the coupling medium, with a sector scanner 33, which can be rotated about itself and is integrated in a central position in the bottom wall 7. By consecutively rotating the sector scanner 33 by a previously fixed angle, such as 2°, and subsequently recording a sector-shaped scanning region 34, reading the two-dimensional digitized image data into a memory area with assignment of a data values corresponding to the position of rotation, a conical volume is made available.

The transporting unit of this example, which is not shown, comprises a computer-controlled stepper motor, a drive shaft coupled with the stepper motor and a ring mount, which extends around the sector scanner 33 and is connected to non-rotationally with the sector scanner 33, the toothed ring non-rotationally engaging a gear wheel disposed on the drive shaft.

FIG. 16 shows the inventive example of FIG. 15 with the sector 33 tilted with respect to the bottom wall 7. As described in the previous examples, the tilting provides additional pointers for confirming a finding.

FIG. 17 shows a further example of the inventive apparatus 1, in which the bottom wall 7 has a disk-shaped central region 35, which is mounted rotatably in the center position and in which a linear scanner (not shown) is integrated, which has a rectangular scanning region 36. By rotating the disk-shaped central region 35 and, with that, the linear scanner by a previously fixed angle, usually amounting to 2°, subsequently scanning and reading the two-dimensional, digitized scanning image into a memory area (not shown) of a single user computer with assignment of a data values corresponding to the position of rotation, a cylindrical scanning volume is made available. The transporting unit of this example comprises a gear wheel, which is aligned parallel to the disk-shaped central region 35 and is connected non-rotationally with the latter.

FIG. 18 shows an example of the inventive apparatus 1 of FIG. 17 with a disk-shaped central region 35 of the bottom wall 7, which is tilted by an angle. As already explained, the recording with a tilted disk-shaped central region 31 provides additional information necessary for evaluating a finding.

The inventive apparatuses 1 enable female breasts 2 to be examined in a rapid and contact-free manner. The examination is reproducible and can be carried out independently by assistant staff without the supervision of a physician during the examination, so that the costs of the examination can be lowered. The evaluation method, which is partly computer controlled, makes it possible to obtain further time-saving indications of pathological symptoms.

On the basis of these indications, subsequent, far-reaching examinations, such as mammography methods are conceivable, with the help of which still unresolved ambiguities can be eliminated.

Furthermore, it is possible to carry out the examination immediately after a mammogram has been taken as a precaution, with the help of which a non pathological condition of the breasts 2 was established. Because of the reproducibility of the examination, the three-dimensional ultrasonic images recorded here can be used as a reference for examinations carried out at a later time, so that, in the case of a deviation from the reference values stored in a data bank, a further indication of pathological structures can be derived.

What is claimed is:

1. A method for examining female breasts by means of ultrasound, for which an ultrasonic transducer is shifted by a transporting unit over a fixed path length between scanning positions for scanning flat layer areas in a stationary scanning position over at least one breast and a three-dimensional ultrasonic image is recorded and stored in an assigned memory unit by shifting consecutively while assigning a data value, corresponding to the respective shifting, to a layer image of an image sequence, the ultrasonic transducer being aligned at a tilting angle with respect to the at least one breast and the assigned tilting angle being stored and three-dimensional ultrasonic images being recorded and stored at least at two different tilting angles, wherein the coordinates of the ultrasonic images, recorded with different tilting angles, are imaged by means of a conversion program, taking into consideration the tilting angles, onto a common coordinate system and compared with one another with a comparison program, direction-dependent structures in the respective three-dimensional ultrasonic images being determined by means of an evaluation program by scanning the image points in the vicinity of a fixed threshold value, compared by subtraction with projection onto the respective scanning direction and structures, occurring only in individual memory areas being discarded as artifacts.

2. The method of claim 1, wherein the gradient of the intensity change and the projection of the direction-dependent area on to the alignment of the ultrasonic beam, fixed by the tilting angle of the ultrasonic transducer, are calculated with the evaluation program.

3. The method of claim 1 or claim 2, wherein the ultrasonic images are compared point by point by forming differences.

* * * * *